United States Patent [19]
Lau et al.

[11] Patent Number: 6,110,340
[45] Date of Patent: Aug. 29, 2000

[54] GEL CASTING AND ELECTROPHORESIS DEVICE

[75] Inventors: Timothy O. Lau, Fremont; Urs Steiner, Sunnyvale; Eric Coates, San Francisco; Thomas S. Acampora, San Jose, all of Calif.

[73] Assignee: Hoefer Pharmacia Biotech, Inc., San Francisco, Calif.

[21] Appl. No.: 09/078,528

[22] Filed: May 13, 1998

Related U.S. Application Data

[60] Provisional application No. 60/046,349, May 13, 1997.

[51] Int. Cl.[7] .................................................. G01N 27/26
[52] U.S. Cl. ........................................ 204/467; 204/619
[58] Field of Search .................................... 204/456, 466, 204/467, 606, 616, 465, 620

[56] References Cited

U.S. PATENT DOCUMENTS

| | | | |
|---|---|---|---|
| 4,857,163 | 8/1989 | Gurske et al. | 204/468 |
| 5,792,332 | 8/1998 | Montecino et al. | 204/618 |

*Primary Examiner*—Jill Warden
*Assistant Examiner*—Alex Noguerola
*Attorney, Agent, or Firm*—Royal N. Ronning, Jr.; Victoria M. Malia

[57] ABSTRACT

The present invention involves a gel casting and electrophoresis device that simplifies the gel cassette casting and electrophoresis process by providing an integral frame assembly that includes a bottom sealing means movable to a first position where the sealing means seals the bottom of the gel cassette for gel casting purposes and a second position which exposes the bottom of the gel cassette for electrophoresis purposes.

25 Claims, 7 Drawing Sheets

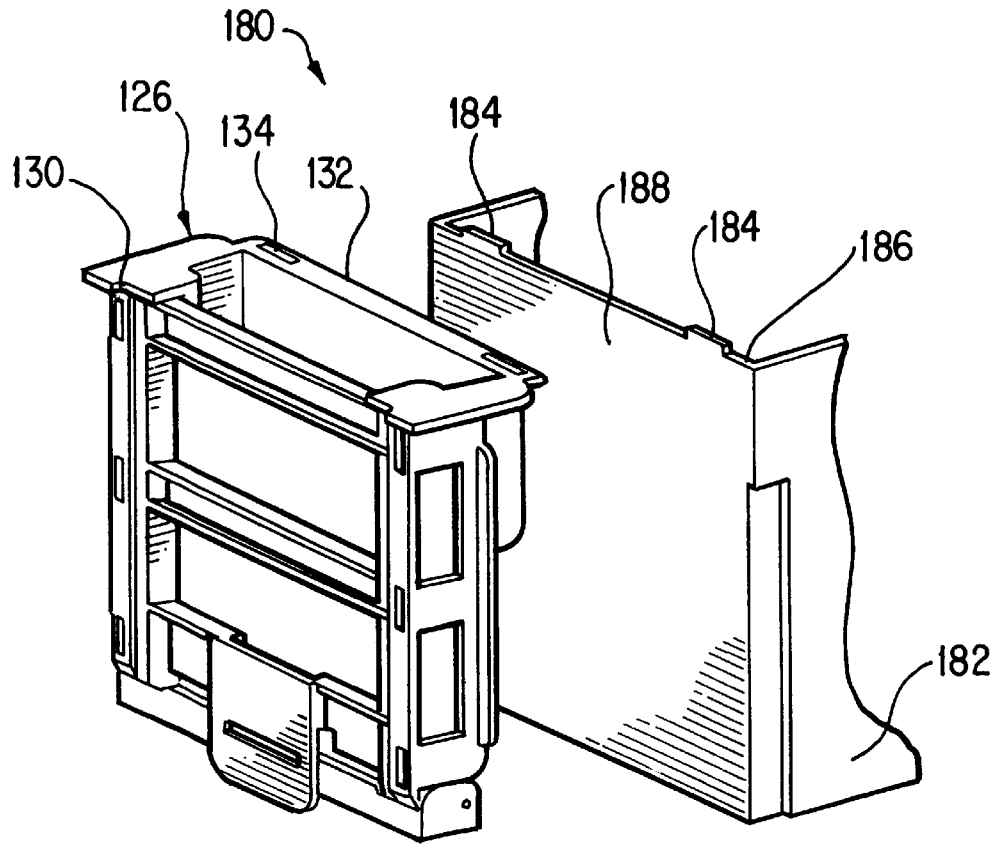
FIG. 6A
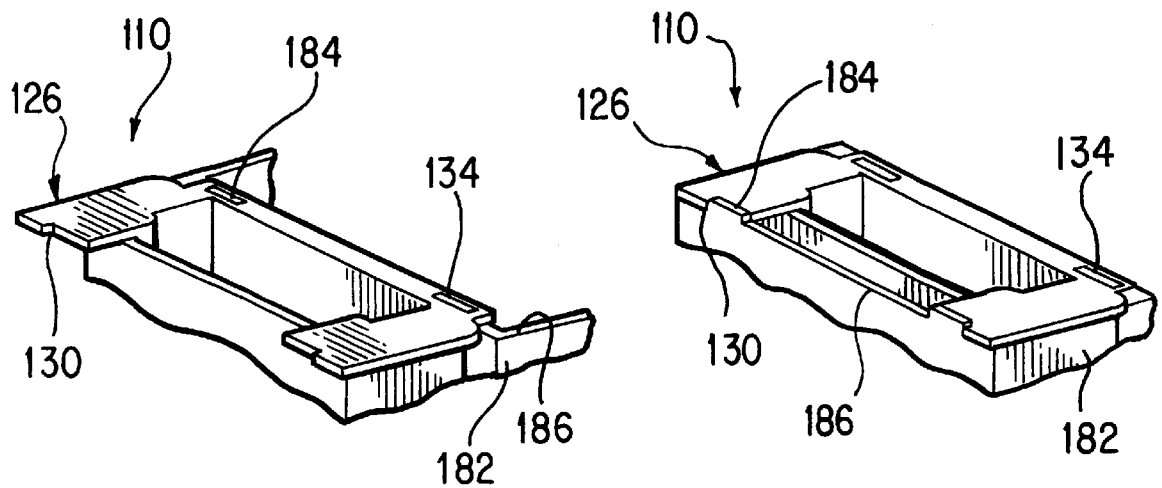
FIG. 6B
FIG. 6C

GEL CASTING AND ELECTROPHORESIS DEVICE

This application claims benefit of provisional application Ser. No. 60/046,349, filed May 13, 1997.

FIELD OF THE INVENTION

The invention relates, in general, to devices used for gel casting and chromatography, and, in particular, to devices used for holding and sealing gel cassettes during vertical gel casting and holding gel cassettes during vertical electrophoresis.

BACKGROUND OF THE INVENTION

It is a common practice in biological experimentation to separate proteins and nucleic acids, e.g., DNA, for analytical and preparative purposes using electrophoresis. During electrophoresis, molecules are separated according to their relative mobilities through a polymer network or gel under the influence of electric potentials.

Electrophoresis is performed by applying one or more samples to one end of a thin slab of the gel, e.g. hydrogel matrix such as polyacrylamide or agarose, and an electric potential is applied to the gel for a certain period of time inducing charged components of the samples to move in parallel directions for various distances. The migration distances depend on the relative mobilities of the components which in turn depend on their sizes and chemical natures. During or after the period of electrophoresis, the location of the various components in the gel are determined using autoradiography, fluorescent detection, or any other well known means for identifying the components.

Most users prepare gels as they are needed, i.e., handcast gels, rather than purchase commercially prepared gels, i.e., pre-cast gels, for reasons of experimental flexibility and cost. Preferably, polymerization or casting of gels is performed utilizing a liquid-tight mold or cassette. This is especially critical for polymerizing polyacrylamide if the gels are formed as thin, vertical slabs. A leak during polymerization may result in a gel that is too short to be of any use.

The most commonly-used vertical gel cassette comprises a pair of rectangular glass plates, i.e., an inner and an outer plate, each having a top edge, a bottom edge and sides. The plates are spaced apart by spacers along the sides of the plates, between the inner and outer plates. The spacers comprise flat, narrow strips of sealing material. The plates and spacers define a an internal volume of the cassette with an open top edge and open bottom edge. The inner plate often has a lower top edge than the outer plate to facilitate electrical contact between the top edge of the gel and an electrode via a buffer contained in an upper buffer chamber.

Vertical gel cassettes are made liquid-tight by securely clamping the glass plates against the spacers along the sides of the cassette and sealing the bottom edge of the cassette with separate sealing mechanisms. The bottom edge is sealed by any of a number of means such as inserting a solid bottom spacer, applying a thin layer of rapid-gelling material such as agarose to the bottom, sealing the bottom with a water-resistant adhesive tape, or pressing the bottom edge against an elastomeric surface.

Once the cassette has been assembled and the bottom sealed, a mixture of monomer, catalyst and buffer are introduced into the cassette and allowed to polymerize, i.e., the gel is cast. A well-forming comb can be inserted in the top edge of the mixture so that multiple individual test sample wells are formed during polymerization.

After polymerization, the separate sealing mechanisms are removed from the bottom edge of the cassette to provide electrical access to the bottom surface of the gel, and the well-forming comb is removed from the top edge of the gel.

The gel cassette is then transferred to an electrophoresis apparatus and electrically coupled with an upper electrode through a buffer medium contained in the upper buffer chamber and with a lower electrode through a buffer medium contained in a lower buffer chamber or tank.

Using conventional techniques, the sealing and casting are performed in a separate apparatus and/or location from the apparatus and location in which the electrophoretic separation is performed. Performing the sealing and casting in a separate apparatus and/or location complicates the sealing, casting, and electrophoresis procedure because the gel cassette has to be transferred from one holding apparatus and/or location to another and numerous separate parts related to the sealing, casting, and electrophoresis must be managed.

SUMMARY OF THE INVENTION

The present invention is directed toward a gel casting and electrophoresis device that simplifies the gel casting and electrophoresis process by providing an integral frame assembly that includes a sealing mechanism that is movable to a first position where the sealing mechanism seals an edge of the gel cassette for gel casting purposes and a second position where the sealing mechanism does not obstruct the edge of the gel cassette so that the bottom edge can contact a buffer medium for electrophoresis.

In a preferred embodiment of the present invention, the gel casting and electrophoresis device is used for vertical gel casting, and the edge of gel cassette is the bottom edge.

In a preferred embodiment of the present invention, the integrated frame assembly includes an upper buffer chamber adapted to receive a buffer medium.

In a preferred embodiment of the present invention, the frame assembly includes an upper buffer chamber and carries a seal around part of the upper buffer chamber for sealingly engaging the gel cassette to the frame assembly around part of the upper buffer chamber.

In a preferred embodiment of the present invention, the sealing mechanism includes a sealing pad.

In a preferred embodiment of the present invention, the frame assembly includes a bottom portion and the sealing mechanism is pivotally connected to the bottom portion of the frame assembly for pivotal movement from the first position to the second position.

In a preferred embodiment of the present invention, the gel casting and electrophoresis device also includes a retaining mechanism for retaining the sealing mechanism in the first position, sealed against the bottom edge of the gel cassette. The retaining mechanism includes a side clamp with a clamp screw, and the side clamp is pivotally connected to the frame assembly.

In a preferred embodiment of the present invention, the frame assembly includes a retaining mechanism adapted to retain the gel cassette to the frame assembly.

In an alternative embodiment of the present invention, an additional retaining frame assembly including a retaining mechanism is provided for retaining the retaining frame assembly and the gel cassette to the frame assembly. The retaining mechanism preferably includes a slot and corresponding side tab adapted to engage the slot or a flexible clamp portion adapted to clamp onto the frame assembly.

In an alternative preferred embodiment of the present invention, the gel casting and electrophoresis device also includes a pair of side clamps for retaining the gel cassette to the frame assembly and maintaining a seal along the sides of the gel cassette.

In a further embodiment of the present invention, the gel casting and electrophoresis device includes an additional retaining frame assembly having a retaining mechanism for retaining the gel cassette to the frame assembly and maintaining a seal along the sides of the gel cassette.

Another aspect of the present invention involves a support mechanism for supporting the gel casting and electrophoresis device on, and outside of, a lower buffer chamber assembly.

In a preferred embodiment of the support mechanism of the present invention, the support mechanism includes a tenon and mortise arrangement.

A further aspect of the present invention involves a method of casting a gel and performing electrophoresis, including the steps of providing a gel cassette with a bottom edge; providing an integrated frame assembly adapted to hold the gel cassette, the frame assembly including an upper buffer chamber adapted to receive a buffer medium and a sealing mechanism, the sealing mechanism movable from a first position for sealing the bottom edge of the gel cassette for gel casting to a second position where the sealing mechanism does not obstruct the bottom edge of the gel cassette so that the bottom edge can contact a buffer medium for electrophoresis; loading the gel cassette on the integrated frame assembly; moving the sealing mechanism to the first position so as to seal the bottom edge of the gel cassette; casting a gel in the gel cassette; loading a test sample in the gel; moving the sealing mechanism to the second position so that the sealing mechanism does not obstruct the bottom edge of the gel cassette; providing the bottom edge of the gel cassette in a buffer medium so that the bottom edge contacts the buffer medium; and performing electrophoresis on the gel.

A still further aspect of present invention involves a method of casting a gel, comprising the steps of providing a gel cassette having a bottom edge; providing an integrated frame assembly adapted to hold the gel cassette, the gel cassette having a bottom edge, the frame assembly including an upper buffer chamber adapted to receive a buffer medium and a sealing mechanism adapted to seal the bottom edge of the gel cassette for gel casting; loading the gel cassette on the integrated frame assembly; sealing the bottom edge of the gel cassette with the sealing mechanism; and casting a gel in the gel cassette.

Other features and advantages of the inventions are set forth in the following detailed description and drawings, which are intended to illustrate, but not limit, the invention.

BRIEF DESCRIPTION OF THE DRAWINGS

FIGS. 2A–2C are perspective views of the components of the gel casting and electrophoresis device of FIG. 1, wherein FIG. 2A shows a frame of the device, FIG. 2B shows a side clamp of the device, and FIG. 2C shows an exemplary bottom edge sealing mechanism of the device;

FIGS. 6A–6C are a perspective view, a partial perspective view, and a partial perspective view, respectively, of the gel casting and electrophoresis device of FIGS. 5A–5C and a lower buffer tank, and show a support mechanism constructed in accordance with another aspect of the invention, for supporting the gel casting and electrophoresis device on, and outside of, the lower buffer tank.

DESCRIPTION OF THE PREFERRED EMBODIMENTS

Figure 1:
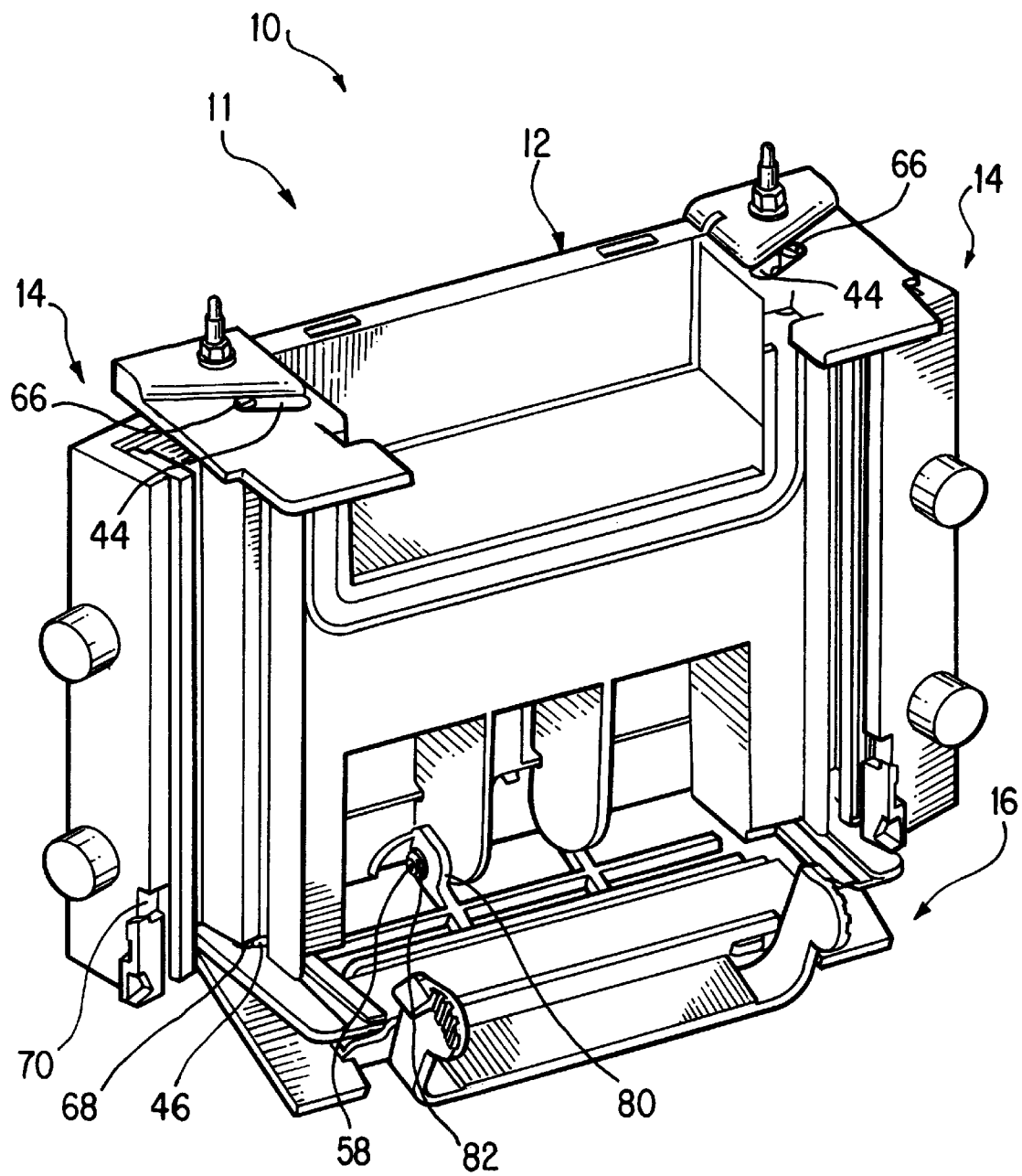
FIG. 1 is a perspective view of a gel casting and electrophoresis device constructed in accordance with a preferred embodiment of the present invention.
Figure 2A:
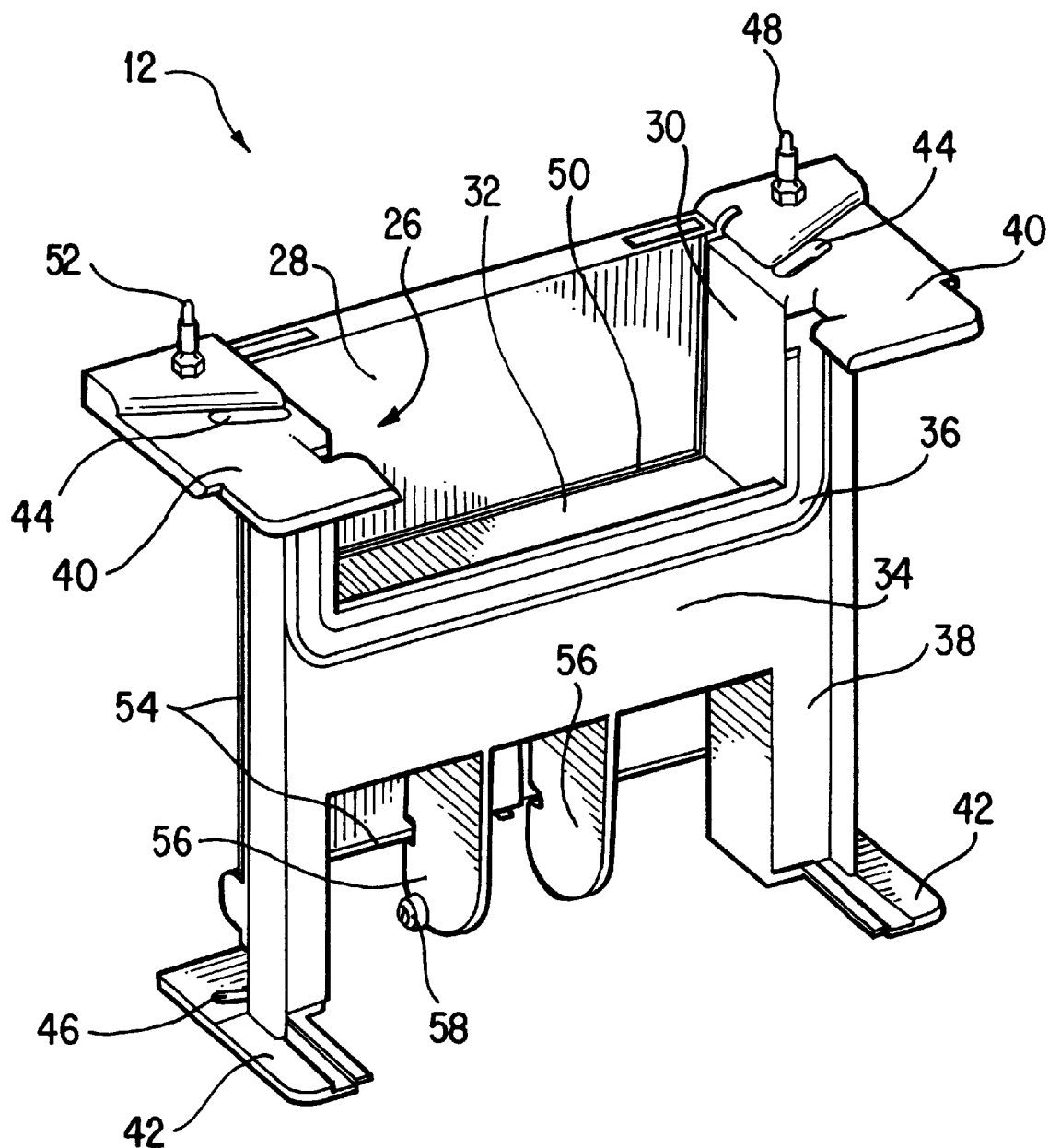
Figure 2B:
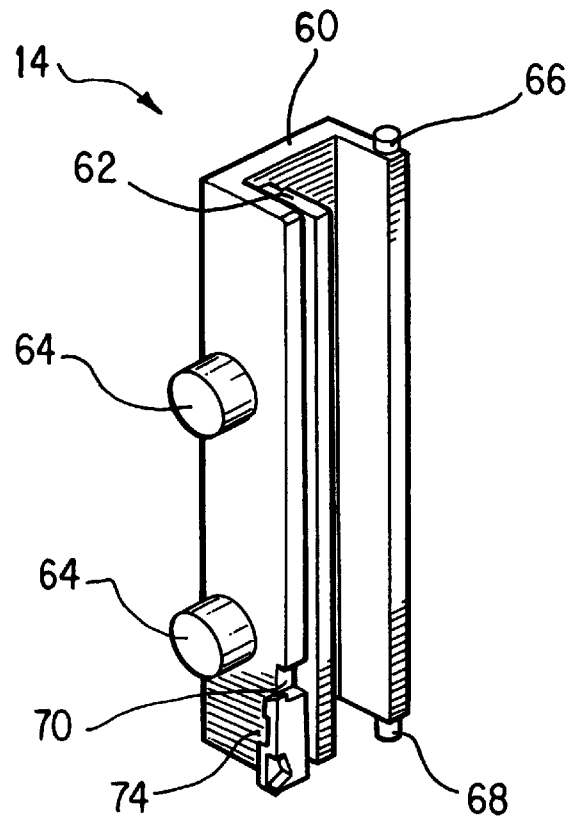
Figure 2C:
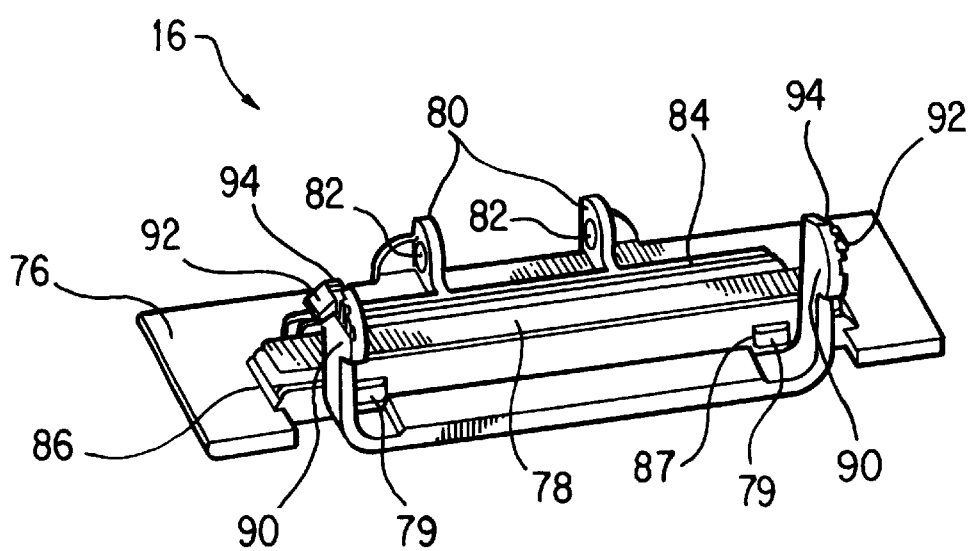
Figure 3:
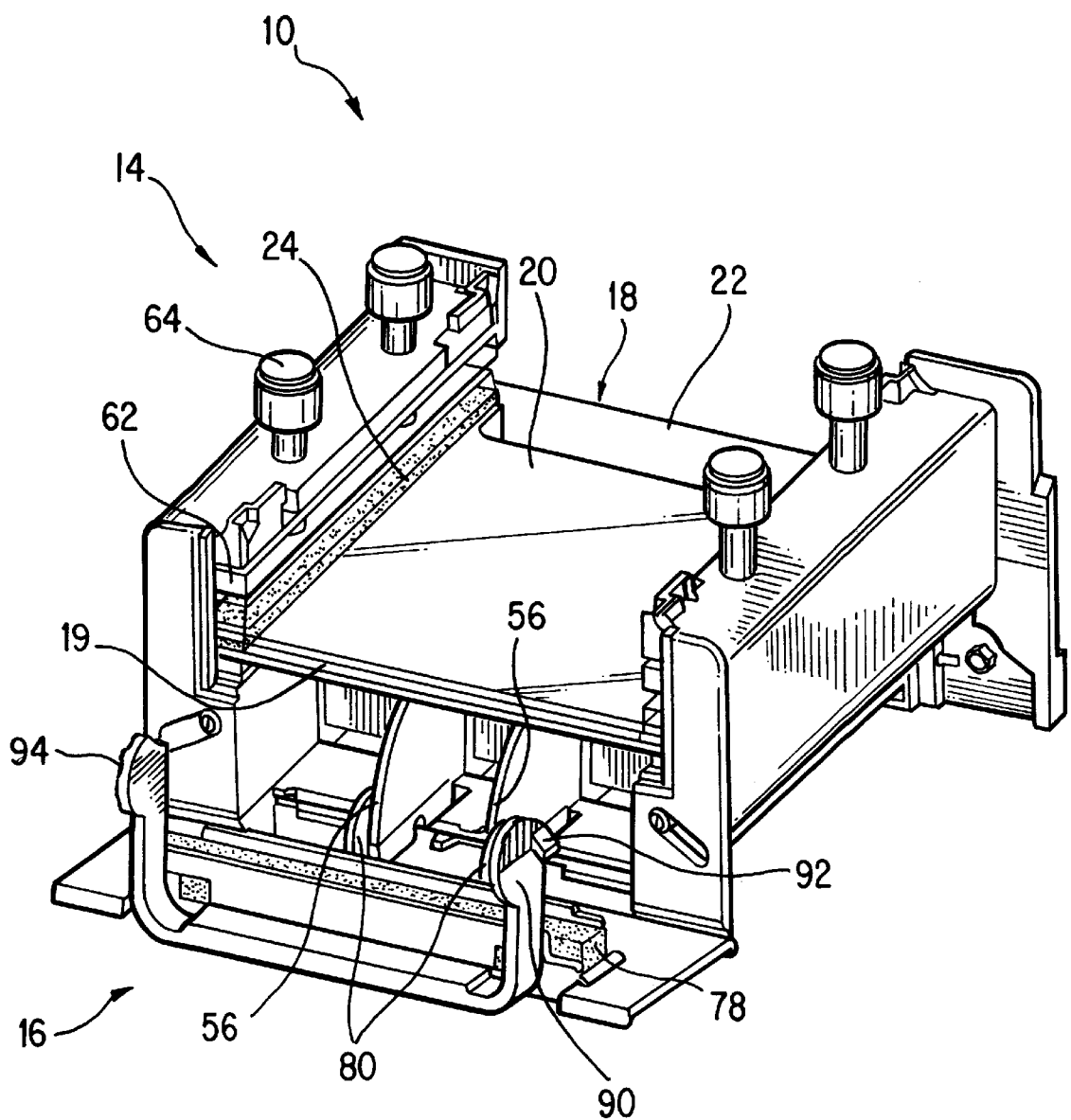
FIG. 3 is a perspective view of the gel casting and electrophoresis device of FIG. 1 shown in conjunction with a gel cassette.

With reference to FIGS. 1–3, a gel casting and electrophoresis device 10, in accordance with a preferred embodiment of the invention, will now be described. The gel casting and electrophoresis device 10 comprises an integrated upper buffer chamber frame assembly 11 including a frame 12, a pair of side clamps 14 pivotally connected to the frame 12, and a bottom edge sealing mechanism 16 pivotally connected to the frame 12.

The gel casting and electrophoresis device 10 holds a pre-cast or handcast gel cassette 18 (FIG. 3) for vertical gel casting and electrophoresis. Although the device 10 can be used with a pre-cast or handcast gel cassette 18, the device 10 will be described in conjunction with a handcast gel cassette 18 because a handcast gel cassette requires sealing along a bottom edge 19. The gel cassette 18 includes inner and outer rectangular plates 20, 22, respectively, spaced and sealed along its sides by side sealing spacers 24 disposed between the inner and outer plates 20,22. Plates 20, 22 can be made using, for example, glass, polycarbonate, or other materials that are well known by those skilled in the art. The spacers 24 comprise relatively or substantially flat, narrow strips of sealing material which can be made of glass, plastic, or other materials that are well known by those skilled in the art. The plates 20, 22 and spacers 24 define an internal volume of the cassette 18 with an open top edge and open bottom edge. The inner plate 20 often has a lower top edge than the top edge of the outer plate 22 to facilitate electrical contact between the top edge of a gel, e.g., a polymerized mixture of monomer, catalyst and buffer, disposed within the internal volume of the cassette 18 and an electrode via a buffer contained in an upper buffer chamber.

Although the gel casting and electrophoresis device 10 is described in a preferred embodiment in conjunction with the gel cassette 18, it will be readily appreciated by those skilled in the art that the present invention may be used with other cassettes having a different configuration that require an edge other than a bottom edge to be sealed for gel casting. For example, in another embodiment of the cassette 18, gel loading may not occur along a top edge, e.g., side edge or bottom edge to prevent air bubbles from forming in the gel cassette, of the cassette and sealing may be required along a different edge than the bottom edge 19, e.g. top edge, side edge.

With reference specifically to the embodiment illustrated in FIG. 2A, an upper portion of the upper buffer chamber frame 12 includes an upper buffer chamber 26 bounded by a back wall 28, end walls 30, a bottom surface 32, and a lowered front wall 34. The frame 12 is made of an injection molded plastic. a front surface of the front wall 34 includes a groove that carries an U-shaped elastomeric sealing gasket 36 made of a soft silicone foam rubber. When the cassette 18 is in place on the frame 12 (FIG. 3), the sealing gasket 36 forms a water-tight seal with the outer surface of the inner plate 20 so that buffer medium does not leak from the upper buffer chamber 26.

The frame 12 includes vertical supports 38 on opposite sides of the frame 12. At an upper portion of the frame 12, the supports 38 include respective upper side flanges 40. At a lower portion of the frame 12, the supports 38 include respective lower side flanges 42. The upper and lower side flanges 40, 42 include upper and lower side clamp pivot slots 44, 46, respectively.

One of the upper flanges 40 carries an upper electrode connector 48, which can be electrically connected to an upper electrode 50 located in the upper buffer chamber 26. An opposite flange 40 carries a lower electrode connector 52, which can be electrically connected to a lower electrode 54 located along the lower portion of the frame 12.

The lower portion of frame 12 also includes a pair of vertically extending pivot supports 56 that receive pivot pins 58 for pivotally connecting the bottom edge sealing mechanism 16 to the lower portion of the frame 12.

With reference specifically to the embodiment illustrated in FIG. 2B, the side clamps 14 comprise a clamp body 60 having a U-shaped cross-section, a pressure plate 62, and clamp screws 64 for exerting and releasing uniform pressure on the sides of the gel cassette 18 via the pressure plate 62. The pressure plate 62 is preferably made of a rigid plastic material; however, other materials can be used. The clamp body 60 includes upper and lower pivot pins 66, 68, respectively, that are received by the upper and lower pivot slots, 44, 46, respectively, for pivotal and sliding movement of the side clamps 14. The clamp body 60 includes a sealing position notch 70 and an open position notch 74 at a lower portion of the body 60. The open position notch 74 cooperates with a retaining latch 92, to be described, (FIG. 2C) for retaining the sealing mechanism 16 in an open position, off the floor of the lower buffer chamber or tank during electrophoresis.

With reference specifically to the embodiment illustrated in FIG. 2C, the bottom edge sealing mechanism 16 comprises a sealing base plate 76 and compressible sealing pad 78 having side tabs 79. The sealing pad 78 is made of an elastomeric silicone rubber material. a pair of pivot supports 80 extend from one side of the base plate 76. The pivot supports 80 include respective pivot holes 82 for receiving the pivot pins 58 at the bottom of the frame (FIG. 2A). The sealing pad 78 is restrained on the base plate 76 by longitudinal restraining ribs 84, lateral restraining ribs 86, and side slots 87 in the longitudinal restraining ribs 84 that cooperate with the side tabs 79 to restrain the sealing pad 78. Spring tabs 90 extend from an opposite side of the base plate 76 from the pivot supports 80. Each spring tab 90 terminates in a latch 92 and ribbed finger grip 94.

The gel casting and electrophoresis device 10 can be manufactured, in general, by injection molding the frame 12, side clamp bodies 14, and sealing base plate 76 out of a rigid plastic material, applying the relevant subcomponents, e.g., electrodes 50, 54, connectors 48, 52, sealing gasket 36, etc., and attaching the side clamps 14 and sealing mechanism 16 to the frame 12 to form an integrated frame assembly 11. The side clamps 14 are attached to the sides of the frame 12 by inserting upper pivot pins 66 in upper pivot slots 44 and lower pivot pins 68 in lower pivot slots 46. The bottom edge sealing mechanism 16 is attached to the lower portion of the frame 12 by inserting the pivot pins 58 through the pivot holes 82 of the pivot supports 80.

Figure 4:
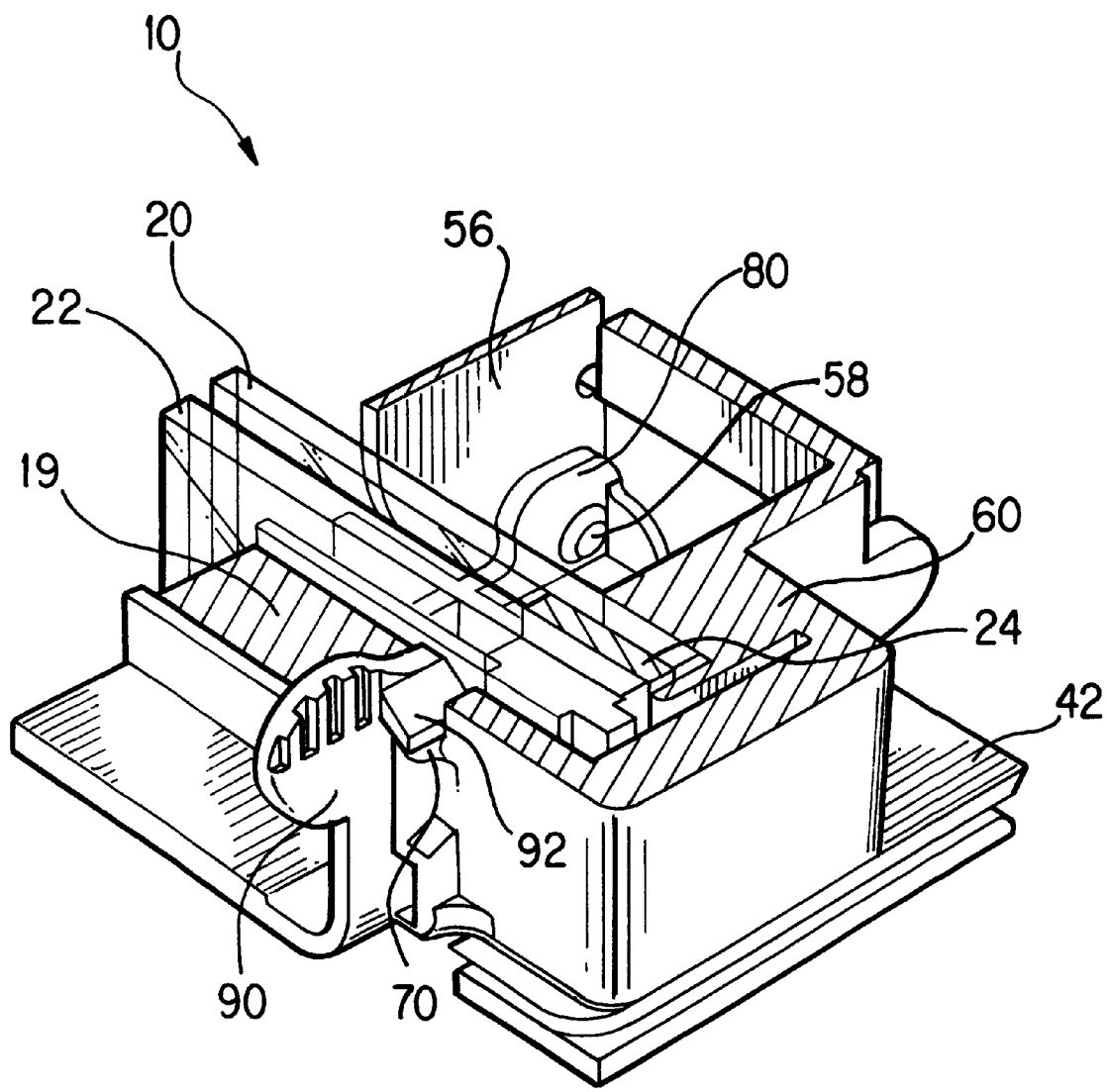
FIG. 4 is a partial, cross-sectional view of a bottom corner portion of the gel casting and electrophoresis device of FIG. 1 in conjunction with a gel cassette.

With reference to FIGS. 1, 3 and 4, the process for assembling, casting, and performing electrophoresis on the gel cassette 18 will now be described. The plates 20, 22 are spaced apart by the spacers 24 along the sides and between the plates 20, 22 to form the framework of the cassette 18. The frame 12 is preferably laid horizontally and the plates 20, 22 are positioned in the frame 12 so that the outer surface of the shorter inner plate 20 contacts the sealing gasket 36.

The bottom edges of the inner glass plate 20, spacers 24, and outer glass plate 22 are aligned flush by pressing the edges against the upper surface of the lower side flanges 42. The side clamps 14 are then pivoted and clamped onto the sides of the cassette 18 through pressure exerted by the clamp screws 64 of the pressure plate 62. Preferably, the amount of pressure exerted is sufficient to seal the sides of the cassette 18 and hold the cassette components in alignment.

The sealing mechanism 16 is then moved to a first, sealing position for sealing the bottom edge 19 of the cassette 18 for gel casting. This is accomplished by pivoting the sealing base plate 76 and inserting the latches 92 into the sealing notches 70 of the side clamps 14 (FIG. 4). The latches 92 and sealing notches 70 form a retaining mechanism for retaining the sealing mechanism 16 in the first, sealed position. In the sealed position, the sealing pad 78 is held under sufficient pressure against the bottom edge 19 of the gel cassette 18 to seal the bottom edge 19 of the gel cassette 18.

Once the cassette 18 has been assembled and sealed, the frame 12 is preferably positioned vertically, and a mixture of monomer, catalyst and buffer are introduced at the top edge into the cassette 18 and allowed to polymerize, i.e., the gel is cast. Before polymerization, a well-forming comb can be inserted into the top edge of the gel mixture to create sample wells in the top edge of the gel. After casting the gel, the comb is removed from the top edge of the gel and the sample wells are filled with a test sample and a buffer medium.

As mentioned above, in an alternative gel cassette embodiment, the cassette may have a different configuration and the gel mixture may be introduced at a location of the gel cassette other than the top edge.

After casting the gel, the bottom sealing mechanism 16 is moved to a second, un-sealed position, where the sealing mechanism 16 does not obstruct the bottom edge 19 of the gel cassette 18, to provide electrical access to the bottom surface of the gel. This is accomplished by disengaging the retaining mechanism by pinching together the spring tabs 90 using finger grips 94 until the latches 92 are unobstructed by the sealing notches 70, and pivoting the sealing base plate 76 away from the bottom edge 19 of the cassette 18.

The gel casting and electrophoresis device 10 with gel cassette 18 is then transferred to an electrophoresis lower buffer chamber or tank. The gel cassette 18 is electrically coupled with the upper electrode 50 through an upper buffer medium contained in the upper buffer chamber 26 and with the lower electrode 54 through a lower buffer medium contained in the lower buffer chamber or tank. The device 10 is covered with a safety lid, and electrophoresis is performed, causing the molecules of the test sample to be separated according to their relative mobilities through the polymer network under the influence of the electric potential.

It will be readily appreciated by those skilled in the art that alternative bottom edge sealing mechanisms or means, which are integral with the frame assembly 11, could be used to seal the bottom of the gel cassette 18 in a manner similar to that described above. For example, but not by way of limitation, a pivot and snap mechanism, similar to the sealing mechanism described above, could be employed that pivots from the front of the frame and snaps to the back of frame. Alternatively, a sliding dam device could be used that moves along a sloping track having periodic anti-reverse detents so that the dam rises against the bottom of the cassette to seal it, yet is movable to an unobstructed position for electrophoresis. By alternative example, a cam system may be employed which brings a dam or other sealing piece into sealing contact with the bottom of the cassette by rotation of at least one cam in one direction and removes the dam from the bottom of the cassette by rotation of the cam in an opposite direction.

The use of a gel casting and electrophoresis device comprising an integrated frame assembly having a gel cassette bottom sealing mechanism eliminates the need for tape or a separate casting stand for preparing a single gel for electrophoresis. In addition, the gel casting and electrophoresis process is simplified by the present invention because the user no longer has to cast the gel in a separate casting unit and/or location and then transfer it to a separate electrophoresis holding unit and/or location.

Figure 5A:
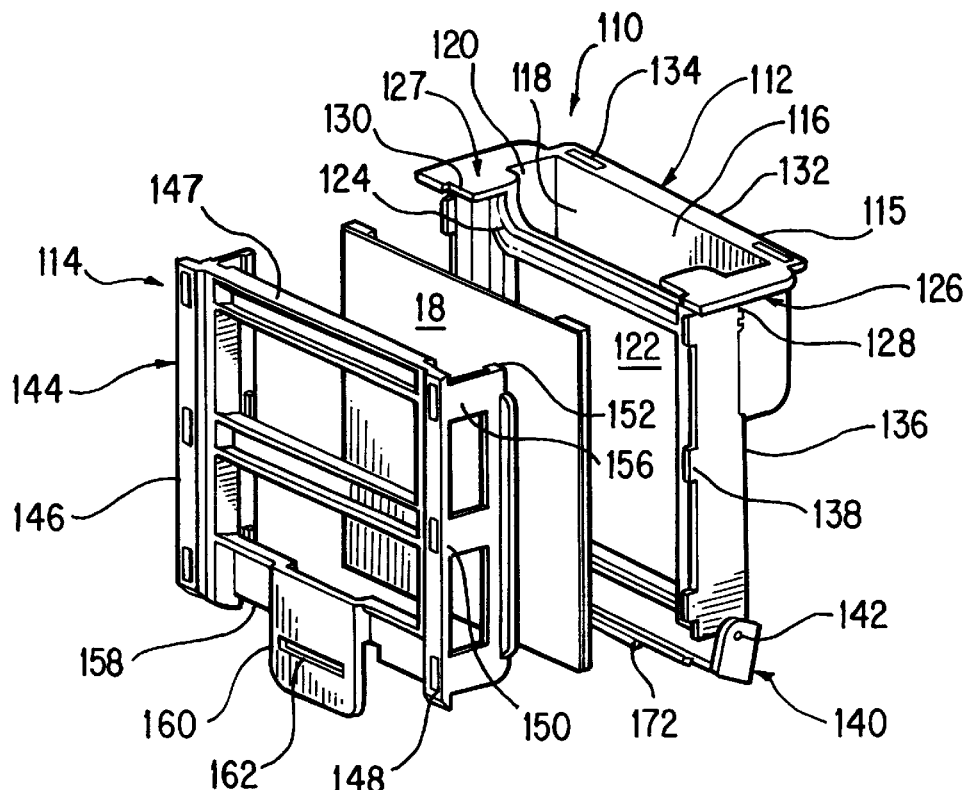
FIGS. 5A–5C are an exploded perspective view, a perspective view, and an enlarged partial perspective view, respectively, of a gel casting and electrophoresis device constructed in accordance with a further embodiment of the present invention shown in conjunction with a gel cassette.
Figure 5B:
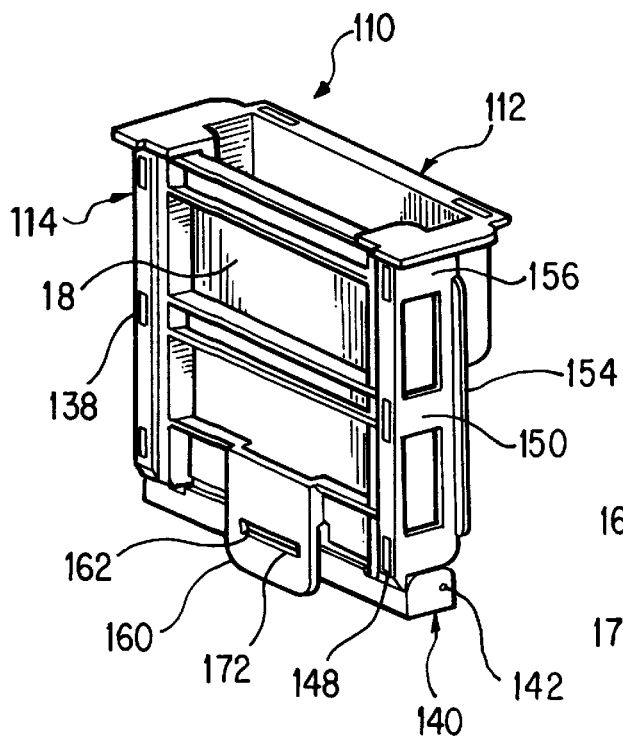
Figure 5C:
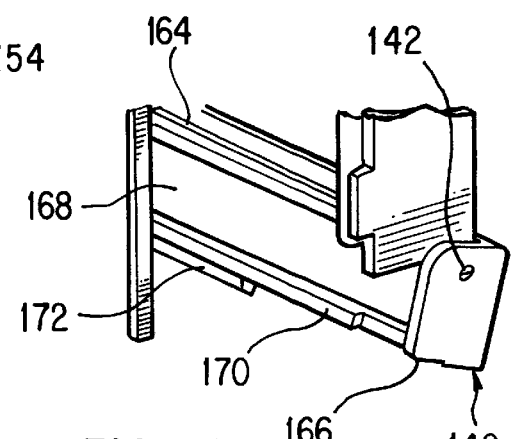

With reference to the embodiment of FIGS. 5A–5C, a gel casting and electrophoresis device 110 constructed in accordance with an additional embodiment of the invention is shown. Similar to the gel casting and electrophoresis device 10 described above, the present device 10 can be used with both pre-cast gel cassettes and handcast gel cassettes, but is described in conjunction the handcast gel cassette 18 described above because this frequently used type of cassette requires sealing along the bottom edge of the cassette 18. However, after reading this description, it will become apparent to one skilled in the art how to use this embodiment with pre-cast gel cassettes.

The gel casting and electrophoresis device 110 in this embodiment comprises a main frame assembly 112 and a retaining frame assembly 114. The main frame assembly 112 includes an upper buffer chamber frame 115 having an upper buffer chamber 116 in an upper portion of the frame 115. The buffer chamber 116 is bounded by a back wall 118, end walls 120, a lowered front wall 122, and a bottom surface. The front surface of the lowered front wall 122 carries a sealing gasket 124.

The top of the frame 115 includes a flange portion 126 extending outwardly from a substantial part of the upper outer periphery of the buffer chamber 116. The flange portion 126 includes side flanges 127, front cut-out 130, and rear flange 132. The rear flange 132 includes mortises 134 near opposite sides of the rear flange 132.

The frame 115 includes vertical supports 136 near the end walls 120. Tabs 138 extend outwardly from a front edge of the supports 136. a sealing mechanism 140, to be described, is pivotally connected to a bottom portion of the supports 136 by pivot pins 142.

The retaining frame assembly 114 comprises a retaining frame 144 with vertical supports 146 and transverse supports 147. The vertical supports 146 include slots 148 spaced vertically the same distance as the distance between the aforementioned tabs 138. Flexible clip members 150 extend from the vertical supports 146. Vertical clip portions 152 extend inwardly from the ends of the respective clip members 150 and vertical ribs 154 extend outwardly from the ends of the respective clip members 150. a bottom transverse support 158 includes a flexible snap mechanism 160 with a snap slot 162.

The bottom edge sealing mechanism 140 includes a sealing base plate 164 with pivot supports 166 extending from opposite ends of the plate 164. The pivot supports 166 include respective pivot holes that receive the pivot pins 142. a compressible sealing pad 168 is fixed to the base plate 164, restrained by longitudinal ribs 170. a longitudinal snap head 172 extends from a central portion of the base plate 164.

In order to hold the gel cassette 18 to the main frame assembly 112 for gel casting and electrophoresis, the gel cassette 18 is positioned between the main frame assembly 112 and retaining frame assembly 114, and the retaining frame assembly 114 is clipped to the main frame assembly 112. This is accomplished by clipping the tabs 138 of the main frame assembly 112 into the slots 148 of the retaining frame assembly 114, and clamping the clip portions 152 of the retaining frame assembly 114 to the rear edges of the supports 136 of the main frame assembly 112. In an alternative embodiment of the invention, the retaining mechanism comprises only a tab 138 and slot 148 arrangement on the clip portions 152 in conjunction with the rear edges of the supports 136.

In order to seal the bottom edge sealing mechanism 140 to the bottom edge 19 of the gel cassette 18, the sealing base plate 164 is pivoted to a first, sealing position, where the sealing pad 168 contacts the bottom edge 19 of the gel cassette, and the snap head 172 of the sealing mechanism 140 is snapped into the snap slot 162 of the snap mechanism 160. The snap head 172 and snap slot 162 form a retaining mechanism for retaining the sealing mechanism 140 to the bottom of the gel cassette 18 with sufficient sealing pressure for casting the gel.

After casting the gel, the snap head 172 is disengaged from the snap slot 162 by pulling on the flexible snap mechanism 160, and pivoting the sealing mechanism 140 to a second position where the sealing mechanism 140 does not obstruct the bottom edge 19 of the gel cassette 18 from contacting a buffer medium during electrophoresis.

With reference to FIGS. 6A–6C, a preferred embodiment of a support mechanism 180 for supporting the gel casting and electrophoresis device 110 on, and outside of, a lower buffer chamber assembly or tank 182 in accordance with an additional aspect of the present invention is shown. The support mechanism 180 includes a mortise and tenon arrangement comprising the above-described mortises 134 located in the rear flange 132 of the device 110 and a pair of corresponding tenons 184 extending from an upper edge 186 of a wall 188 of the tank 182.

The gel casting and electrophoresis device 110 is supported on, and outside of, the tank 182 by placing the mortises 98 of the device 110 over the tenons 184 of the wall 188. The gel casting and electrophoresis device 110 is provided in this supported position during casting of the gel, and during test sample loading.

During electrophoresis, the gel casting and electrophoresis device 110 is placed in the tank 182 and supported by the flange portion 126 on the upper edge 186 of the tank wall 188. The cut-outs 130 of the flange portion 126 accommodate the tenons 184 of the tank 182.

The above-described support mechanism is desirable for users that prefer the gel casting and electrophoresis device to be more stable for gel holding, casting, sample loading, and for keeping the gel casting and electrophoresis device adjacent to the tank for convenience purposes.

It will readily appreciated by those skilled in the art that other support mechanisms could be used to support the gel casting and electrophoresis device on, and outside of, the tank. For example, but not by way of limitation, the support mechanism may include a clip that slides onto the wall 188 of the tank 182 to support the device 110, or a peg and hole arrangement.

It will also be readily apparent to those skilled in the art how some of the features described herein, such as the support mechanism may be applied to other embodiments or aspects of the invention, such as the gel casting and electrophoresis device 10.

Although this invention has been described in terms of certain preferred embodiments, other embodiments apparent to those of ordinary skill in the art are also within the scope of this invention. Accordingly, the scope of the invention is intended to be defined only by the claims that follow.

We claim:

1. A gel casting and electrophoresis device, comprising:
    an integrated frame assembly adapted to hold a gel cassette, the gel cassette having an edge, the frame assembly including a sealing mechanism, the sealing mechanism movable from a first position for sealing said edge of the gel cassette for gel casting to a second position where the sealing mechanism does not obstruct said edge of the gel cassette so that said edge can contact a buffer medium for electrophoresis.

2. The device of claim 1, wherein the gel casting and electrophoresis device is for vertical gel casting and electrophoresis.

3. The device of claim 1, wherein said edge is a bottom edge of the gel cassette.

4. The device of claim 1, wherein the integrated frame assembly includes an upper buffer chamber adapted to receive a buffer medium.

5. The device of claim 4, wherein the frame assembly carries a seal around part of the upper buffer chamber.

6. The device of claim 1, wherein the sealing mechanism includes a sealing pad.

7. The device of claim 1,.wherein the frame assembly includes a bottom portion, the sealing mechanism is pivotally connected to the bottom portion of the frame assembly for pivotal movement from the first position to the second position.

8. The device of claim 1, further including a retaining mechanism adapted to retain the sealing mechanism in the first position.

9. The device of claim 1, wherein the frame assembly includes a retaining mechanism adapted to retain the gel cassette to the frame assembly.

10. The device of claim 9, wherein the retaining mechanism includes a side clamp with a clamp screw, and the side clamp is pivotally connected to the frame assembly.

11. The device of claim 10, wherein the retaining mechanism for the sealing mechanism includes a notch in the side clamp and corresponding latch on the sealing mechanism.

12. The device of claim 1, further including a retaining frame assembly having a retaining mechanism, that retains the retaining frame assembly and the gel cassette to the frame assembly.

13. The device of claim 12, wherein the retaining mechanism includes a slot and corresponding side tab adapted to engage the slot.

14. The device of claim 13, wherein the retaining mechanism includes a flexible clamp portion adapted to clamp onto the frame assembly.

15. The device of claim 1, further including a support mechanism adapted to support the frame assembly on, and outside of, a lower buffer chamber assembly.

16. The device of claim 15, wherein the support mechanism includes a mortise and tenon arrangement.

17. The device of claim 1, wherein the gel cassette is a pre-cast gel cassette.

18. A gel casting and electrophoresis device, comprising:
    an integrated frame assembly adapted to hold a gel cassette, the gel cassette having a bottom edge, the frame assembly including an upper buffer chamber adapted to receive a buffer medium and means for sealing the bottom edge of the cassette for gel casting, the sealing means movable from a sealing position for gel casting to a non-sealing position where the sealing mechanism does not obstruct the bottom edge of the gel cassette so that the bottom edge can contact buffer medium for electrophoresis.

19. A gel casting and electrophoresis device, comprising:
    an integrated frame assembly adapted to hold a gel cassette, the frame assembly having an upper portion, a bottom portion, and opposite sides, the gel cassette having a bottom edge, the frame assembly including an upper buffer chamber adapted to receive a buffer medium, a pair of side clamps pivotally connected to the opposite sides of the frame assembly for retaining the gel cassette to the frame assembly, and a sealing mechanism pivotally connected to the bottom of the frame assembly for pivotal movement from a first position for sealing the bottom edge of the gel cassette for gel casting to a second position where the sealing mechanism does not obstruct the bottom edge of the gel cassette so that the bottom edge can contact a buffer medium for electrophoresis, and a retaining mechanism adapted to retain the sealing mechanism in the first position, the sealing mechanism including a notch in each of the side clamps and respective latches on the sealing mechanism adapted to engage the notches.

20. The device of claim 19, wherein the side clamps each include a clamp screw.

21. The device of claim 19, further including a support mechanism adapted to support the frame assembly on, and outside of, a lower buffer chamber.

22. The device of claim 21, wherein the support mechanism includes a mortise and tenon arrangement.

23. A gel casting and electrophoresis device, comprising:
    an integrated frame assembly adapted to hold a gel cassette, the gel cassette having a bottom edge, the frame assembly including an upper buffer chamber adapted to receive a buffer medium and a sealing mechanism adapted to seal the bottom edge of the gel cassette for gel casting.

24. A method of casting a gel and performing electrophoresis, comprising:
    providing a gel cassette having a bottom edge;
    providing an integrated frame assembly adapted to hold the gel cassette, the frame assembly including an upper buffer chamber adapted to receive a buffer medium and a sealing mechanism, the sealing mechanism movable from a first position for sealing the bottom edge of the gel cassette for gel casting to a second position where the sealing mechanism does not obstruct the bottom edge of the gel cassette so that the bottom edge can contact a buffer medium for electrophoresis;
    loading the gel cassette on the integrated frame assembly;
    moving the sealing mechanism to the first position so as to seal the bottom edge of the gel cassette;
    casting a gel in the gel cassette;
    loading a test sample in the gel;
    moving the sealing mechanism to the second position so that the sealing mechanism does not obstruct the bottom edge of the gel cassette;
    providing the bottom edge of the gel cassette in a buffer medium so that the bottom edge contacts the buffer medium; and performing electrophoresis on the test sample through the gel.

25. A method of casting a gel, comprising:

providing a gel cassette having a bottom edge;

providing an integrated frame assembly adapted to hold the gel cassette, the gel cassette having a bottom edge, the frame assembly including an upper buffer chamber adapted to receive a buffer medium and a sealing mechanism adapted to seal the bottom edge of the gel cassette for gel casting;

loading the gel cassette on the integrated frame assembly;

sealing the bottom edge of the gel cassette with the sealing mechanism; and casting a gel in the gel cassette.

* * * * *